United States Patent [19]

Silvanov

[11] Patent Number: 4,950,223
[45] Date of Patent: Aug. 21, 1990

[54] STOMA CLOSURE DEVICES

[75] Inventor: Beverley Silvanov, London, Great Britain

[73] Assignee: Trimark (R&D) Limited, Great Britain

[21] Appl. No.: 241,600

[22] Filed: Sep. 7, 1988

Related U.S. Application Data

[63] Continuation-in-part of Ser. No. 46,873, Sep. 5, 1986, abandoned.

[30] Foreign Application Priority Data

Sep. 5, 1985 [GB] United Kingdom ............... 85 22037

[51] Int. Cl.$^5$ ............................................ A61J 1/00
[52] U.S. Cl. ............................. 600/32; 128/DIG. 25
[58] Field of Search ............................. 604/332–345; 128/DIG. 25; 600/29–32

[56] References Cited

U.S. PATENT DOCUMENTS

| 2,324,520 | 7/1943 | Lamson | 600/32 |
| 4,210,132 | 7/1980 | Perlin | 600/30 |
| 4,850,953 | 7/1989 | Haber et al. | 604/32 |

FOREIGN PATENT DOCUMENTS 3613696 10/1987 Fed. Rep. of Germany ........ 600/32

Primary Examiner—Jerome L. Kruter
Attorney, Agent, or Firm—Ostrolenk, Faber, Gerb & Soffen

[57] ABSTRACT

A closure device for use in the closure of stomas and the like is described and comprises a bellows like reservoir which is integral with and in fluid communication with a bell-shaped inflatable bung. The inflatable bung can be positioned with a body channel of the stoma and inflated to a predetermined degree defined by the volume of the reservoir. A filter channel is provided in an annular ring of the device and is positioned so as to permit escape of flatus without becoming blocked by liquid or solid materials from the body channel.

16 Claims, 6 Drawing Sheets

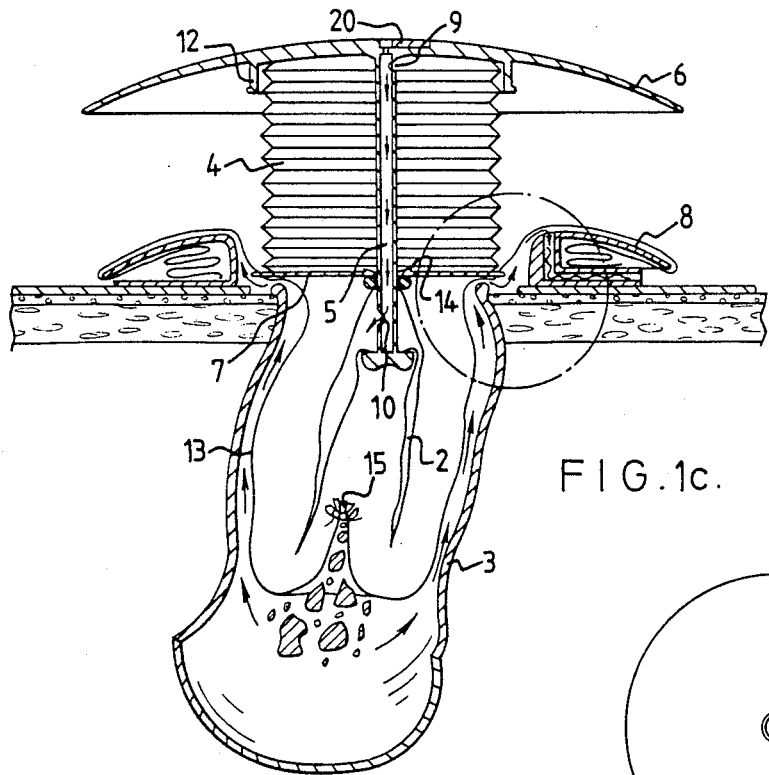
FIG.1c.
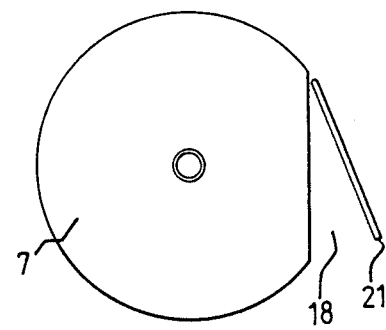
FIG.1d.
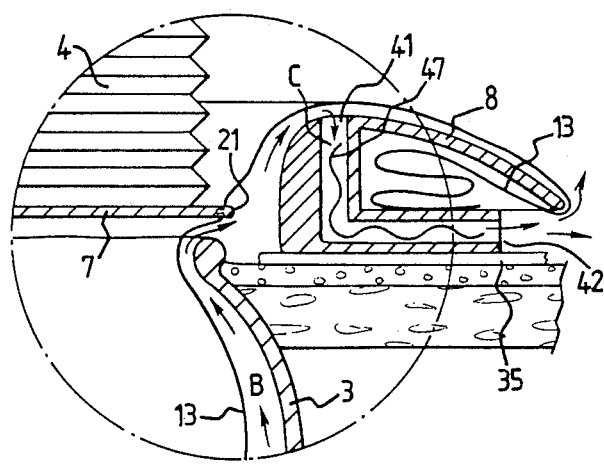
FIG.1e.
FIG.1f.

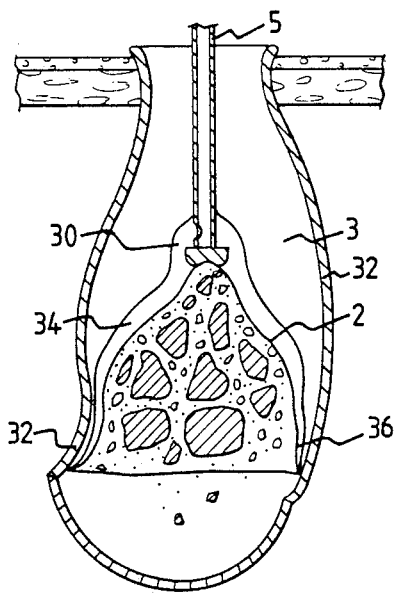
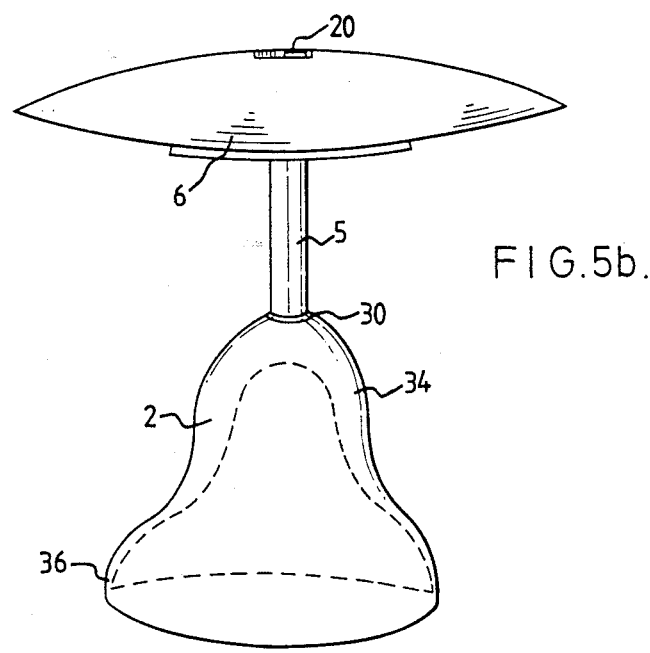
FIG.5a.
FIG.5b.

STOMA CLOSURE DEVICES

CROSS-REFERENCE TO RELATED APPLICATION

This is a continuation-in-part application of U.S. patent application Ser. No. 046,873 filed on Sept. 5, 1986 now abandoned.

FIELD OF THE INVENTION

This invention relates to closure devices for use in the closure of body channels, and in particular but not exclusively, to the closure of stomas produced as a result of ileostomy, urostomy, colostomy surgery and the like.

BACKGROUND OF THE INVENTION

Ostomy surgical procedure comprises severage of the intestine and redirection of the intestinal tract to a stoma, which is formed as an artificial opening in the skin. An annular member may be attached or held against the body so that the stoma is aligned within a central aperture of the member. Matter passing out of the stoma and through the aperture is received in a collection vessel supported from and contained in the annular member.

U.S. Pat. No. 2,324,520 (Lamson) describes an apparatus for closing an abnormal opening in the wall of the anatomy, which apparatus comprises an inflatable blocking member to be positioned within a body channel which member is connected to an outer flange supported on the outside surface of the body wall. In order to close the opening, a detachable syringe can be screwed into a valve which cooperates with the blocking member via a channel passing through the wall. By pumping the syringe, the blocking member can be inflated so as to block the body channel.

United Kingdom patent specification No. 2108848B (Prager) describes a stoma closure device which comprises a plug having a duct therein for allowing the passage of air into an inflatable balloon positioned within the body channel in the abdomen. The inflatable balloon can be inflated by a detachable syringe which must be screwed into a valve positioned in communication with the duct. Closure of the body channel is effected by the sides of the inflatable balloon pressing against the sides of the body channel, which body channel is in turn pressed against an annular ring sutured to the inside of the wall of the abdominal cavity.

The closure devices described in both of the above patent specifications suffer severe drawbacks. One of the main drawbacks is that a separate detachable syringe is required which needs to be carried around by the user. The need to carry around additional equipment for permitting inflation or deflation of the closure device can lead to the transmission of infection to the stoma.

Another difficulty is that the need to attach additional equipment to the closure device in order to open or close the device is inconvenient for the user.

Another serious difficulty with the syringes described in these patent specifications is that it is impossible for the user to know precisely how much to inflate the balloon or blocking member in order to establish an adequate seal on the one hand, and without rupturing the body channel on the other hand. In many cases, the body channel is the intestine and so the consequences of under inflation or over inflation of the balloon or blocking member can be very serious.

Spherical pressure may only minimally increase the bung in size in relation to the force such a bung can exert on the intestinal wall or on the material the bung is made from.

This problem is particularly apparent in the case where the closure device is to be worn by elderly, mentally incapacitated, or disabled people who will not be able to judge the degree of inflation. Even sensitive persons will not be able accurately to estimate the degree of inflation on account of the relative insensitivity of the intestine. Over inflation can lead to excessive pinching of the stomach wall between a support portion of the device positioned on the outside of the wall or between an annular ring, which surrounds the body channel and is sutured onto the inside of the stomach wall, and the inflatable device. Over inflation can lead to rupturing of the relatively weak junction between the body wall and intestine.

These problems become more acute during long-term use of such closure devices, because the pinching between the inflatable balloon and the sutured annular ring or support portion of the device can lead to necrosis.

U.S. Pat. No. 4,210,132 (Perlin) describes various types of artificial sphincters for closure of a channel in a patient's body. An annular member may be placed around the intestine at a location within the skin of the patient. The annular member may comprise a plurality of annular magnets. A plug having an outer wall can be positioned within the stoma, the outer wall extending along the entire length of the plug. Closure of the artificial sphincter is effected by pumping the plug with a fluid so that direct and pressured contact is made along the length of the plug/intestine boundary. Closure is effected by virtue of the pressure exerted by the fluid within the plug on the intestine wall. The efficiency of the closure is determined by the degree/amount of contact area.

This arrangement has the disadvantage that an effective seal is only established because of the forced pressure along the entire wall surface boundary between the plug and the intestine. The device is therefore not able to expand or contract sufficiently in order to accommodate bowel movements at any one place of contact. This is problematic especially in the event of bowel spasms.

U.S. Pat. No. 4,372,308 (Steer et al) describes an ostomy bag formed by welding two sheets of non-rigid, soft, plastic film together around a periphery. The bag includes a filter positioned uppermost thereof, that is, at a position which is a little above the stoma when in situ. One of the walls of the bag has an aperture for connection to a body channel. This device is only a collection device and not a closure device.

The purpose of the filter is to filter flatus generated within the body channel and expelled therefrom. The disadvantage with this arrangement is that expelling of flatus generally occurs under pressure which causes fluid and/or solid material to be ejected outwardly from the opening of the body channel. Spattering of such material is such as to project the fluid or solid material directly into the filter so as to cause blocking thereof.

USSR patent No. 1199245 (Belo Gen) describes an alternative filter arrangement for a stoma closure. In this arrangement, a closure device comprises a plug portion which is inserted into the opening, and a head portion which extends along the surface of the patient's exterior wall. A filter material is positioned between a head portion and the wall so as to filter flatus emerging from the stoma.

This arrangement suffers from the disadvantage that the filter quickly becomes blocked owing to fluid and/or solid material emerging from the stoma and immediately blocking the filter thereby preventing expelling of flatus and causing discomfort for the patient.

It is an object of the present invention to overcome the aforementioned problems and to provide a neater, simpler, safer, more comfortable and convenient closure device for body channels.

In particular, it is an object of the present invention to provide a closure device which can be opened by means of inflation or deflation of an inflatable member positioned within the body channel, which means for inflating or deflating the devices is integral with the device and is configured to prevent over or under inflation thereof.

It is a further object of the present invention to provide an inflatable member which can provide an effective seal without exerting excessive pressure on the internal walls of the body channel.

It is a further object of the present invention to provide a filter arrangement for a closure device, which filter arrangement is less prone to becoming blocked, and a closure device which can be coupled to a collection device for collecting waste products from a body channel.

SUMMARY OF THE INVENTION

According to the present invention there is provided a closure device for a body channel, the device comprising an inflatable bung for insertion into said body channel, which bung is provided with an interior void for permitting inflation thereof, a reservoir formed integrally with said device, and means for enabling the passage of fluid between the reservoir and said bung, wherein the volume of said reservoir is preselected so that compression of the reservoir displaces only sufficient fluid into said interior void of said bung so as to seal said body channel without application of undue pressure thereto, and when fully compressed, said reservoir is retained in a collapsed state in said closure device.

The volume of the reservoir is preferably preset by a clinician of the patient, or during manufacture of the device.

Adjustment means may preferably be provided in the reservoir for enabling adjustment of the preset volume according to the physical characteristics of the patient destined to receive the closure device.

Means may be provided for sealing the adjustment means against being tampered with.

The bung is preferably formed of a flexible material having elastic qualities (for example, rubber, an elastomeric material, siliconised rubber or latex, while the reservoir may be formed from a more rigid but collapsible material possibly in the form of a bellows.

Alternatively, both the bung and reservoir may comprise equally elastic materials so that when the user initiates compression of the reservoir, the reservoir continues to collapse so as to fill the bung without further action on behalf of the user. In this case the bung and reservoir are such as to continue the collapse of the bung without further action by the user after the user initiates expansion of the reservoir.

The reservoir may be provided with a cap beneath which the reservoir can collapse so as to fit within a chamber provided in the device, which chamber is suitable for positioning adjacent the stoma.

The device may be provided with means for supporting a film for collecting fluid and/or solid material expelled from the body channel. One end of the film may be positioned within the body channel prior to or after insertion of the bung.

Devices constructed in accordance with the closure device defined above employ a "balanced volume" principle which ensures safety of the patient by permitting the clinician to preset the volume of fluid which may be used to inflate the bung. This leads to a reduced risk of the reservoir or bung bursting due to over inflation. There is also a significantly reduced risk of the possibility of necrosis occurring due to over inflation of the bung during long term use of the device.

The integral nature of the reservoir and bung provides for more comfort for the patient during use of the device since there is no need to carry around additional equipment to provide for inflation or deflation of the bung (that is closing or opening of the device).

A further advantage is that the device can be opened quickly and conveniently without the need to attach additional equipment. This is particularly advantageous in case of emergency when internal bleeding may be occurring and there would be an urgent need for someone to deflate the bung as quickly as possible.

The elimination of a separate pumping device or syringe or valve release mechanism enhances the dignity with which the user can accept the device. Another advantage is that the "balanced volume" principle enables quick inflation so as to prevent spillage which occurs with conventional devices. This advantage is particularly important in a social context.

According to another aspect of the invention, there is provided a bung for use in a closure device for a body channel having side walls, which bung comprises:

a neck portion for connection to a fluid supply capable of inflating the bung, wherein said neck portion has a diameter which is generally less than that of said body channel so that said neck is generally free from contact within said body channel;

a first flared portion which extends from one end of said neck portion and has a resilient character and flares outwardly from said neck portion towards said walls of said body channel; and a contact portion contiguous with an end of said first flared portion remote from said neck defining an open end of said bung, which contact portion is disposed inwardly of said body channel when inserted therein, said contact portion being arranged for contacting said walls of said body channel under influence of a pressure present within said body channel being greater than that outside of said body channel thereby effecting a seal to prevent outflow of fluid, solid material and/or flatus from said body channel.

The bung may be of a foam plastic or rubber material. Preferably, the bung is inflatable so it can be deflated when it is desired to permit escape of material from the body channel and inflated to close the body channel.

The inflatable bung is preferably formed from a flexible elastomeric material.

The contact portion of the inflatable bung is preferably provided with tapered ends having substantially no resilience of their own but sufficient resilience to cling against the wall of the body channel sufficient for effecting a seal.

Bungs constructed in accordance with the above have the advantage that there is an overall reduced surface contact area between the bung and the walls of the body portion. This, coupled with a reduced pressure exerted by the bung on the walls enhances comfort and safety for the user.

The contact portion of the inflatable bung effectively acts as a non-return valve when in contact with the side walls. The natural pressure within the intestine urges the contact portion against the side walls of the body channel or intestine.

Since a relatively small area of contact is necessary in order to effect a seal in embodiments of this invention, the body channel or intestine is free to fluctuate in diameter without the risk of the seal breaking. The seal is sufficiently effective for there to be no real need to use a subcutaneaus sutured annular ring as used in prior art arrangements.

The contact portion is preferably tapered at the open end thereof so as to cling to the wall of the intestine or body channel. This prevents fluid, solid material or flatus passing between the bung and the walls in an outward direction of the body channel.

According to the present invention there is further provided a filter device for a closure and/or disposal device for a body channel, which filter device comprises an annular ring to be positioned around an opening of said body channel onto a surface of a body, said annular ring comprising support means for supporting and/or containing a film material into which fluid and/or solid material ejected from said body channel can be collected, said annular ring comprising a filter channel having a first end which opens into a cavity defined within said film material and is positioned upwards of said opening when in use, and a second end which opens to the outside of said cavity, a portion of said filter channel in the vicinity of said first end being oriented so as to be substantially parallel to said body channel, and wherein said first end is positioned so that, in use, said film hangs over said first end and over said opening of said body channel such as to obstruct said first end, the device being arranged so that impact of fluid and/or solid material expelled from said body channel on to said film in a direction away from said body channel moves said film so as to open said first end and allow flatus moving in a direction substantially opposite to that of said material expelled from said body channel to enter said portion and pass through said filter channel.

Filter devices according to the present invention can process the flatus quickly and efficiently. This prevents the collection film from inflating like a balloon on emission of flatus and other substances from the body channel.

The filter channel is preferably provided with an activated charcoal material for absorbing components of flatus.

In alternative embodiments, the filter channel may extend around the periphery of the annular ring so that a greater quantity of activated charcoal material may be accommodated.

Alternatively, a plurality of separate filter channels may be incorporated into a single annular ring.

Embodiments of the filter according to the present invention have the advantage that they eliminate or at least alleviate the possibility of becoming blocked thereby allowing a more effective escape of flatus.

It is to be noted that embodiments of the present invention are not restricted for use in stomas in human beings. Embodiments may be applied to ileostomy and colostomy surgery not only in humans but also in animals.

It is also noted that devices may be constructed which incorporate the closure device, filter device and generally bell-shaped bung either singularly or in combination.

BRIEF DESCRIPTION OF THE DRAWINGS

The invention will now be further described, by way of example, with reference to the accompanying drawings, in which light reference numerals designate like elements:

FIG. 1c is another illustration of the embodiment of FIG. 1a showing the flow of flatus in more detail;

FIG. 1d is a view of a plate of the bellows of FIG. 1c showing a clip bar for supporting the collection film;

FIG. 1e is a side sectional view of the clip bar of FIG. 1d showing film positioned between the clip and the bar;

FIG. 1f is an exploded view of the portion of FIG. 1c through which the flatus passes;

FIG. 3b illustrates the positioning of a film within a body cavity prior to insertion of the bung and reservoir of FIG. 3a;

FIG. 5a shows a generally bell-shaped bung in accordance with the present invention in an inflated position;

FIG. 5b illustrates the generally bell-shaped bung of FIG. 5a in conjunction with the reservoir according to the present invention;

DETAILED DESCRIPTION OF THE PREFERRED EMBODIMENTS

Figure 1A:
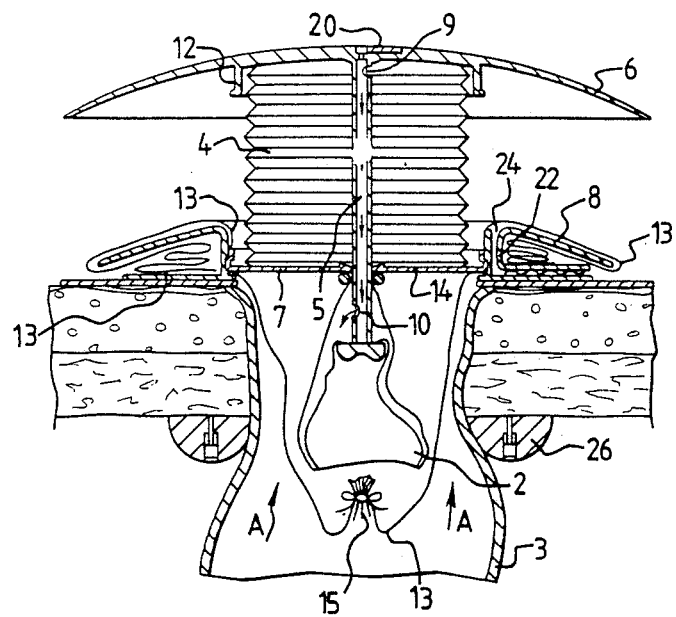
FIGS. 1a and 1b show a closure device, incorporating the "balanced volume" principle, the filter and bell-shaped bung according to the present invention, in an open and closed position respectively.

FIG. 1a illustrates a closure device which comprises a reservoir and bung according to the present invention, a generally bell-shaped bung according to the present invention and a filter channel according to the present invention.

In FIG. 1a, a closure device generally designated by reference numeral 1 comprises an inflatable bung 2 inserted within a body channel 3, which may be the intestine of a human. The device 1 includes a reservoir 4 which is in fluid communication with the interior void of the bung 2 by means of a duct 5.

The bellows itself is formed from a nylon or fibre reinforced plastics material of bellows construction. The bellows part of the reservoir 4 is generally cylindrical, one end being affixed to a cap 6, the other being affixed to a plate 7 which is seated within an annular ring 8 of the device 1. The duct 5 can slidingly and sealingly pass through an 'O' ring 14 provided in the plate 7 when the reservoir 4 is compressed and expanded.

When the user of the device depresses the cap 6, the reservoir 4 collapses so as to urge fluid therein through an aperture 9 positioned in the duct 5. The fluid passes along the duct 5 and exits through an aperture 10 positioned in the vicinity of the interior void of the inflatable bung 2. The inflatable bung 2 therefore inflates so that upon full depression of the cap 6 the bung 2 is fully inflated so as to contact the body channel 3 thereby closing the device (see FIG. 1b). The quantity of fluid within the reservoir is preset by the clinician of the patient so that the correct or appropriate amount of inflation of the bung 2 occurs, taking into consideration the patient's physical characteristics.

When it is desired to open the closure device so as to permit the outflow of fluids, solid materials and flatus from the body channel 3, the cap 6 can be raised so as to expand and inflate the reservoir 4. This in turn causes the bung 2 to collapse thereby allowing passage of the materials in the direction of arrows A illustrated in FIG. 1a.

The device 1 may be retained in a closed state by means of clips 12 which interlock with the inner periphery of the annular ring 8. The annular ring 8 is adhered to the surface of the exterior wall of the patient so as to surround the opening of the body channel 3. The annular ring 8 is adhered by means of karaya gum.

A film 13 for collecting waste material from the body channel 3 is stored within an annular cavity 24 of the generally spool-shaped ring 8. The film 13 is stored in a concertina fashion within the annular cavity 14, the film 13 being generally tubular in nature.

Figure 1B:
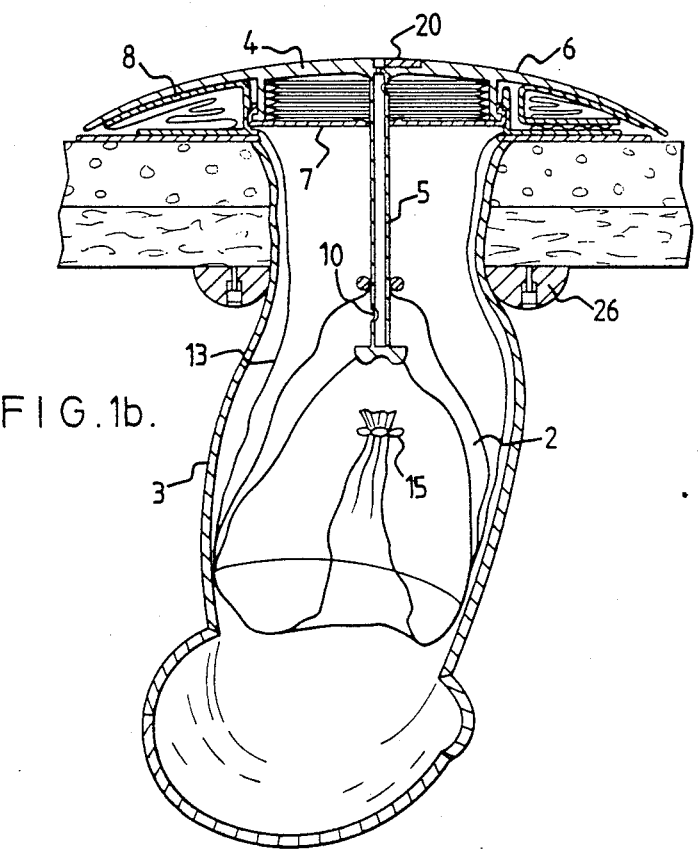
Figure 3A:
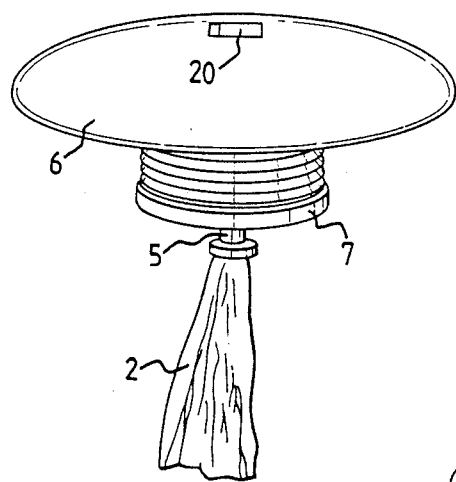
FIG. 3a is a view of an uninflated bung and reservoir embodying the present invention shown before being positioned in a body channel.
Figure 4:
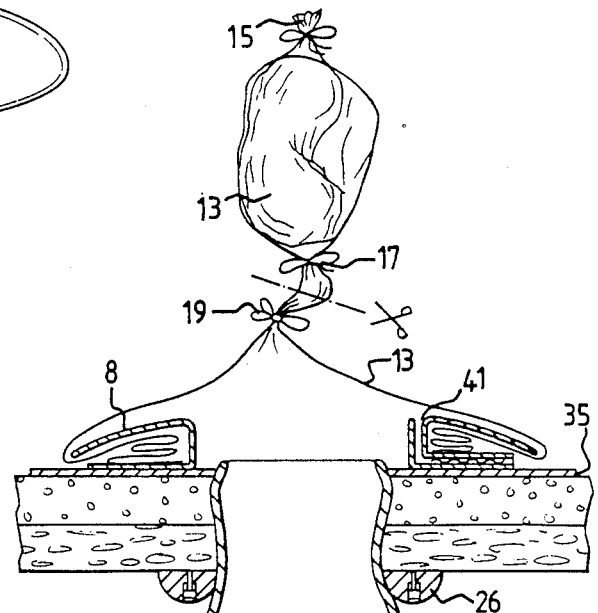
FIG. 4 illustrates the closure device embodying the invention removed from the body channel and shows removal of waste matter collected in the film.
Figure 3B:
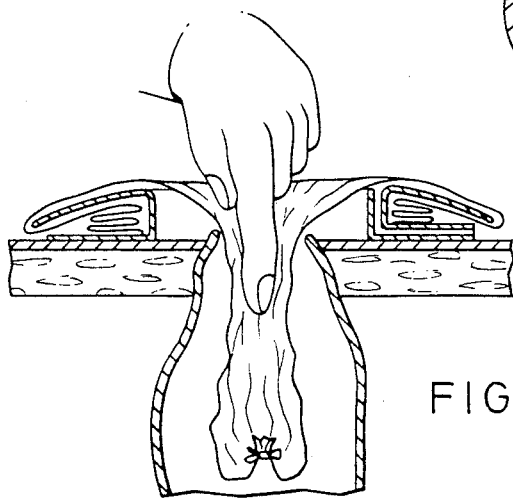

When the device is initially positioned, the annular ring 8 is adhered to the outer surface of the patient's body around the stoma. The film 13 is positioned within the cavity 14 in a concertina like fashion, one end thereof extending from the annular cavity 14. This end 15 is closed and pushed into the body channel 3 as illustrated in FIG. 3b of the accompanying drawings. After insertion of the film 13 into the body channel 3, the bung/bellows assembly (as illustrated in FIG. 3a) is then inserted into the body channel. The device 1 is then closed as illustrated in FIG. 1b until it is desired to remove some fluid, solid material or flatus from the body channel 3. This can be done by opening the device as illustrated in FIG. 1a and as described above. Upon opening of the device in this way, the film 13 within the body channel 3 moves outwardly of the stoma and inverts so as to form a collecting bag which collects the waste material. The bag can then be tied as illustrated in FIG. 4 by means of a tie 17. A further tie 19 is provided in the film extending from the annular cavity 14 and the film is cut between the ties 17 and 19. The film 13 containing the waste material can then be discarded and the film 13 extending from the annular ring 8 can then be pushed into the body channel 3 followed by the bellows/bung arrangement, after which the device is closed as illustrated in FIG. 1b.

FIG. 1c shows the flow of flatus through the filter channel and out of the device. In order to ensure that there is space for the flatus to pass between the plate 7 and the ring 8, an aperture 18 is provided in the plate 7. The film 13 is secured to the plate 7 by a clip bar 21 to stop the film obstructing the flow of flatus (see FIGS. 1d and 1e).

Figure 2A:
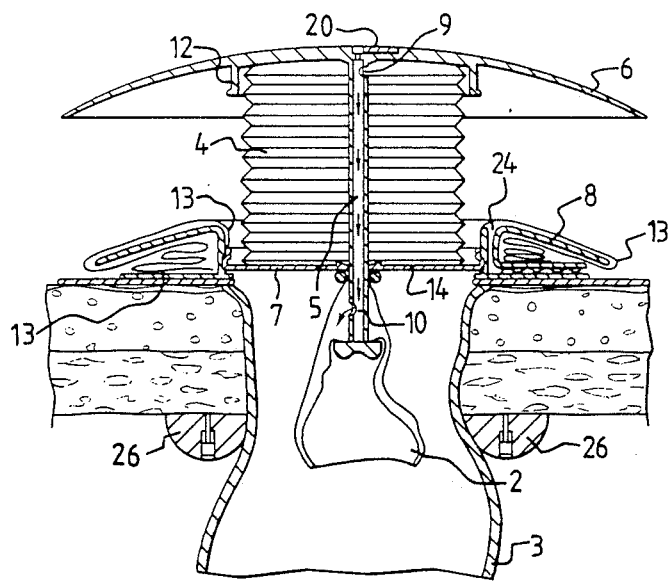
FIGS. 2a and 2b shown an alternative embodiment of closure device, incorporating the present invention, in an open and closed position respectively.
Figure 2B:
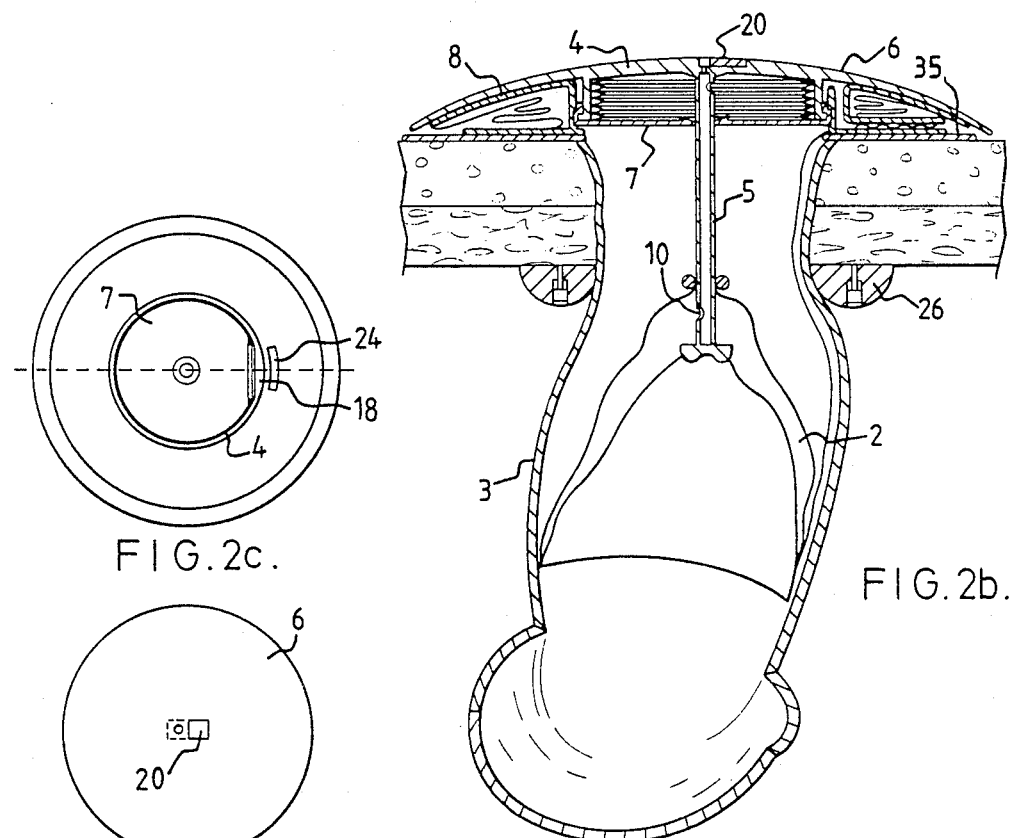

FIGS. 2a and 2b show an alternative arrangement which is similar to that of FIGS. 1a and 1b except that the end of the film 13 which extends from the annular cavity 14 is not tied at 15 as it is in FIG. 1a, but instead is affixed to the plate 7.

In FIG. 2b, a stopper 20 is illustrated, which stopper permits access to the duct and therefore the reservoir 4. Removal of this stopper 20 allows injection or removal of fluid from the reservoir 4 thereby enabling variation of the degree of inflation of the bung 2.

In FIGS. 1a, 1b and 2a and 2b, a filter channel 22 is shown having a charcoal cloth 23 disposed therein. The filter channel 22 has a first opening 24 which opens into the cavity defined by the film 13 and the remainder of the device. In normal use, the film 13 obstructs the first opening 24. The operation of this filter channel will be described below with reference to FIGS. 6 to 9 below.

Figure 2C:
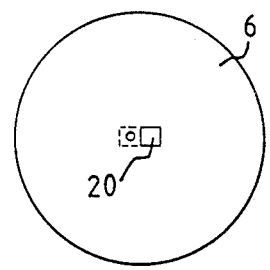
FIG. 2c is a sectional plan view of FIG. 2a with a cap of the reservoir removed.
Figure 2D:
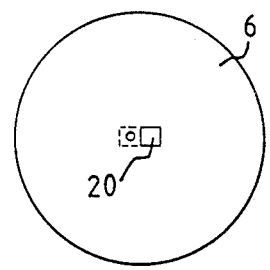
FIG. 2d is a plan view of the cap of FIG. 2c.

FIG. 2c is a plan view of the device of FIGS. 1 and 2 with the cap 6 removed.

Optionally, a ring 26 (FIG. 2b) may be positioned to surround the body channel 3 and may be sutured to the inner abdominal wall of the patient. Such a ring may be present owing to the existence of a previous closure device having been prescribed or used by the patient.

FIG. 5a illustrates a generally bell-shaped bung embodying the present invention. FIG. 5b illustrates the generally bell-shaped bung in association with the bellows type reservoir 4 described with reference to FIGS. 1 and 2.

The generally bell-shaped bung 2 of FIG. 5a is shown positioned within a body channel 3. The bung 2 comprises a neck portion 30 which has a diameter which is less than that of the walls 32 of the body channel 3. The end of the neck 30 which is innermost of the body channel 3 is connected to a flared portion 34 having a resilient or springy character and is also of generally smaller diameter than that of the body channel 3 so that there is generally no contact therebetween during use of the bung 2. A contact portion 36 is provided at the end of the flared portion 34 which is remote front the neck 30. The contact portion tapers in thickness towards its free end to such an extent that it becomes generally filament-like and non-rigid or resilient.

When inflated, the flared portion 34 is in an expanded stated but does not contact the side walls of the body channel 3. A seal is effected between the side walls of the body channel 3 and the contact portion 36 by virtue of pressure within the body channel 3 upstream of the bung 2. This pressure urges the contact portion against the side walls, the contact portion 36 thereby acting like a non-return valve.

Solid waste matter, i.e. faeces, within the body channel 3 can collect within the flared portion of the bung 2 and is compacted into a shape suitable for easy removal from the body channel 3.

The bung 2 is made from a flexible elastomeric material. When it is desired to remove the bung 2 from the body channel 3, the bung is simply deflated so that the flared portions collapse.

Bungs constructed in this manner have the advantage that an effective seal is established by means of a relatively small contact area at the open end of the bung only. The stiffness or resilience of the bung resulting from the fact that the bung 2 is inflated tends to diminish towards the open of the bung at the compact portion 36. The seal is therefore effected by the inherent pressure (from flatus, fluid and solid waste matter) within the gut. The seal effected by this bung has the advantage that bowel movements can be followed more easily owing to the reduced surface contact area between bung and gut wall and by virtue of the fact that the seal results from internal pressure from within the gut or body channel rather than directly from the inflated pressure of the bung 2.

FIG. 5b illustrates the bung of FIG. 5a in conjunction with the bellows type reservoir 4. The reservoir 4 operates in conjunction with the annular ring 8 and the cap 6 as described with reference to FIGS. 1 and 2. The arrangement illustrated in FIG. 5b can be inserted into the body channel 3 after insertion of the film as illustrated in FIG. 3b.

Figure 6:
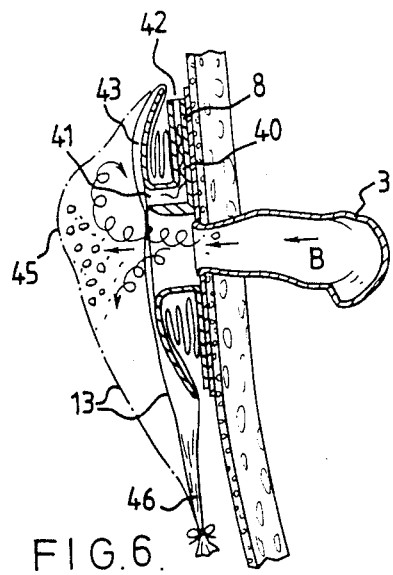
FIG. 6 illustrates a filter channel embodying the present invention.

FIG. 6 illustrates a filter channel which embodies the present invention. In this example, a filter channel 40 is provided in the annular ring which, when in use, is adhered to the patient's wall around the opening of the body channel 3. The ring 8 may be adhered to the body wall by means of karaya gum 35 or other suitable adhesive. The filter channel 40 has first and second ends 41 and 42 respectively. The annular cavity 14 of the ring 8 stores the film in the concertina like fashion described above with reference to FIGS. 1 and 2. The first end 41 opens into a portion 43 of the filter channel which lies substantially parallel to the longitudinal axis of the body channel 3. The first end 41 is positioned in relation to the surface of the annular ring 8 which is disposed generally parallel to the patient's abdominal wall (when the ring is in use) so that the film 13 tends to hang over the first end 41 and the opening of the body channel 3 when in use as illustrated in FIG. 6. The positioning of the first end 41 is such that the film 13 obstructs the opening.

The filter channel 40 provides for the escape of flatus in the following manner. Fluid and/or partially solid material is expelled from the body channel 3 in the direction of arrow B generally under pressure by virtue of flatus present in the body channel. Since the film 13 is close to the opening of the body channel 3 the fluid and/or partially solid material strikes the bag 13 thereby causing the bag 13 to move into the position illustrated by dotted lines in FIG. 6 owing to the inertia of the fluid and/or partially solid material and or pressure of the flatus. Movement of the bag 13 into this position results in opening of the first end 41 of the filter channel 40 thereby permitting the outflow of flatus through the filter channel 40 and out of the second end 42 into the ambient astmosphere.

The relative positioning of the film 13 with respect to the first end 41 and the opening of the body channel 3 is such that solid and/or fluid material expelled from the body channel 3 is restrained from being spattered into the vicinity of the first end 41. Since the portion of the filter channel 43 lies in a direction substantially parallel to the flow direction indicated by arrow B, the fluid and/or solid material is unable to change direction in order to enter the portion 43 of the filter channel 40 and so block the filter channel.

Once the fluid and/or solid material or partially solid material has struck the bag 13 in the zone 45 as indicated in FIG. 6, it generally adheres at least momentarily to the bag 13 and then slides down into the collecting region 46. When in use, the filter channel 40 is disposed generally upward of the opening of the body channel 3.

Figure 7:
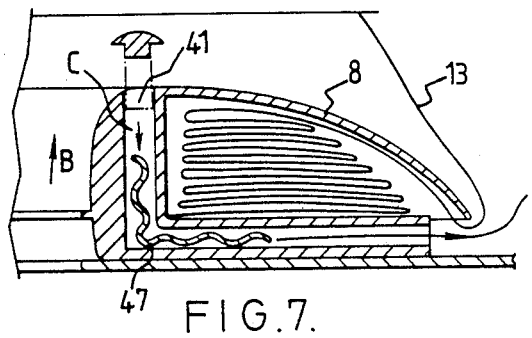
FIG. 7 shows the embodiment of filter channel embodying the present invention in more detail.

FIG. 7 illustrates a more detailed sectional view of the filter channel 40 which may be provided in the annular ring 8. In FIG. 7, the annular ring 8 is shown to be positioned around the opening of the body channel 3. The bag 13 is shown as extending from the ring 8 but untied at the free end. Arrow C illustrates the direction of flow of flatus into the filter channel 40. A piece of cloth 47 is provided for absorbing components of the flatus so as to remove odors contained therein. The filter material preferably comprises an activated charcoal cloth which may be, for example, a conventional charcoal cloth similar to the one disclosed in United Kingdom patent specification No. 1301101. The filter cloth 47 may form a serpentine path within the filter channel 40 as illustrated in FIG. 7. This causes turbulence in the flatus thus washing it several times over.

Figure 8A:
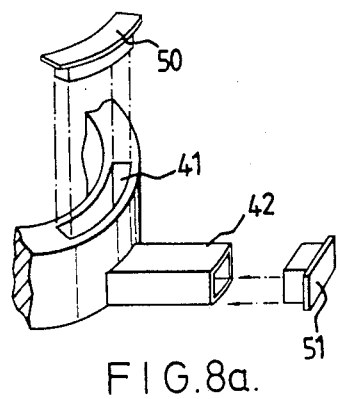
FIGS. 8a to 8c show alternative implementations of filter channel in accordance with the present invention.

FIG. 8a illustrates an alternative form of filter channel 40 which comprises a stopper 50 for the first end 41 and a second stopper 51 for insertion into the second end 42. In this case, the filter channel 40 may be used simply as a chimney, there being no filter material therein. The stoppers can be inserted to prevent the escape of flatus when escape is not desired. The stoppers can be removed in order to permit the escape of flatus at desired times. The stopper can be inserted over the film 13 in the interests of hygiene.

Figure 8B:
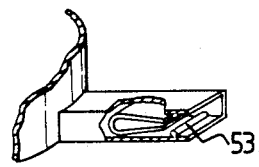

In FIG. 8b, the filter channel 40 is provided with a folded piece of charcoal cloth. Projections 53 are provided along the length of the filter channel 40 in order to cause turbulence of the flatus in order to ensure absorption of oderons gases contained therein.

Figure 9:
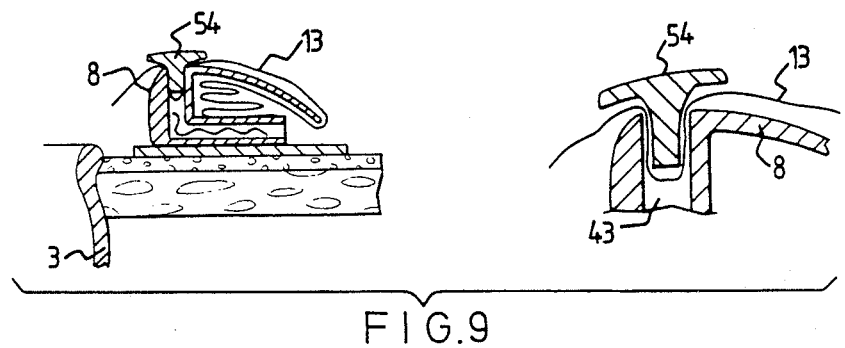
FIG. 9 illustrates a stopper for a filter channel which may be used with or without a film.

FIG. 9 illustrates how a stopper 54 may be provided for insertion into the end 41 of the filter channel so as to enable the patient to control the escape of flatus. The stopper 54 may be inserted into the end 41 over the portion of film 13 which extends over the end 41.

Figure 8C:
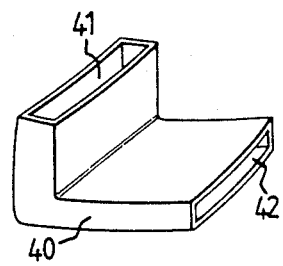

It is to be noted that the filter channel arrangements described with reference to FIGS. 7 to 9 may be used with or without the bung and reservoir arrangement described above.

I claim:

1. A closure device for a body channel, the device comprising an inflatable bung for insertion into said body channel, which bung is provided with an interior void for permitting inflation thereof, a reservoir formed integrally with said device, and means for enabling the passage of fluid between the reservoir and said bung, wherein the volume of said reservoir is preselected so that compression of the reservoir displaces only sufficient fluid into said interior void of said bung so as to seal said body channel without application of undue pressure thereto, and when fully compressed, said reservoir is retained in a collapsed state in said closure device.

2. A closure device according to claim 1 comprising adjustment means for enabling the adjustment of said preset volume according to the physical characteristics of the patient destined to receive said closure device.

3. A closure device according to claim 1, wherein the reservoir is formed from a plastics material in the form of a bellows, and the bung is formed of a flexible material having elastic qualities.

4. A closure device according to claim 1, wherein said bung and said reservoir are formed from materials of substantially equal elasticity so that when the user initiates compression of said reservoir, said reservoir continues to collapse so as to fill said bung without further action on behalf of the user, and said reservoir continues to expand so as to deflate said bung without further action on behalf of the user when the user initiates expansion of said reservoir.

5. A closure device according to claim 1, wherein said reservoir can collapse so as to fit within a chamber provided in said closure device.

6. A closure device according to claim 1, wherein means is provided for supporting and/or containing a film for collecting fluid and/or solid material or partially solid material expelled from said body channel.

7. A closure device according to claim 1, further comprising:

a neck portion for connection to a fluid supply capable of inflating the bung, wherein said neck portion has a diameter which is generally less than that of said body channel so that said neck portion is generally free from contact with said body channel;

a first flared portion which extends from one end of said neck portion and has a resilient character and flares outwardly from said neck portion towards said walls of said body channel when said inflatable bung is inflated and positioned within said body channel; and a contact portion contiguous with an end of said first flared portion remote from said neck defining an open end of said inflatable bung, which contact portion is disposed inwardly of said body channel when inserted therein, said contact portion being arranged for contacting said walls of said body channel under influence of a pressure present within said body channel being greater than that outside of said body channel thereby effecting a seal to prevent outflow of fluid, solid material and/or flatus from said body channel.

8. A closure device according to claim 7 comprising a filter device, which filter device comprises an annular ring to be positioned around an opening of said body channel onto a surface of a body, said annular ring comprising support means for supporting and/or containing a film material into which fluid and/or solid material ejected from said body channel can be collected, said annular ring comprising a filter channel having a first end which opens into a cavity defined within said film material and is positioned upwards of said opening when in use, and a second end which opens to the outside of said cavity, a portion of said filter channel in the vicinity of said first end being oriented so as to be substantially parallel to said body channel, and wherein said first end is positioned so that, in use, said film hangs over said first end and over said opening of said body channel such as to obstruct said first end, the device being arranged so that impact of fluid and/or solid material expelled from said body channel on to said film in a direction away from said body channel moves said film so as to open said first end and allow flatus moving in a direction substantially opposite to that of said material expelled from said body channel to enter said portion and pass through said filter channel.

9. A bung for use in a closure device for a body channel having side walls, which bung comprises:

a neck portion having a diameter which is generally less than that of said body channel so that said neck portion is generally free from contact with said body channel;

a first flared portion which extends from one end of said neck portion and has a resilient character and flares outwardly from said neck portion towards said walls of said body channel; and a contact portion means contiguous with an end of said first flared portion remote from said neck portion defining an open end of said bung, which contact portion is disposed inwardly of said body channel when inserted therein, said contact portion being provided with a tapered distal end means which has substantially no flexibility of its own but of sufficient resilience to cling against said walls of said body channel under influence of a pressure present within said body channel being greater than that outside of said body channel, said contact portion thereby acting as a non-return valve and effecting a seal to prevent outflow of fluid, solid material and/or flatus from said body channel.

10. A bung according to claim 9, wherein said bung is inflatable so it can be deflated when it is desired to permit escape of material from said body channel and inflated to close said body channel.

11. A bung according to claim 9 wherein said neck portion is arranged for connection to a fluid supply which is capable of inflating said bung.

12. A bung according to claim 9 wherein said bung is formed of foam plastic.

13. A bung according to claim 12 wherein said tapered end of said contact portion tapers away from said first portion to such an extent that said tapered end becomes generally filament-like and non-rigid.

14. A bung according to claim 9 wherein said first portion includes a bell shaped inner wall and a bell shaped outer wall, said inner wall being located between said neck portion and said contact portion, said outer wall being located between said neck portion and said contact portion, said outer wall surrounding said inner wall, said outer wall being arranged such that there is generally no contact between said outer wall and said channel during use of said closure device.

15. A filter device for a closure device for a body channel, which filter device comprises an annular ring to be positioned around an opening of said body channel onto a surface of a body, said annular ring comprising support means for supporting and/or containing a film material into which fluid and/or solid material ejected from said body channel can be collected, said annular ring comprising a filter channel having a first end which opens into a cavity defined within said film material and is positioned upwards of said opening when in use, an a second end which opens to the outside of said cavity, a portion of said filter channel in the vicinity of said first end being oriented so as to be substantially parallel to said body channel, and wherein said first end is positioned so that, in use, said film hangs over said first end and over said opening of said body channel such as to obstruct said first end, the device being arranged so that impact of fluid and/or solid material expelled from said body channel on to said film in a direction away from said body channel moves said film so as to open said first end and allow flatus moving in a direction substantially opposite to that of said material expelled from said body channel to enter said portion and pass through said filter channel.

16. A filter device according to claim 15 comprising an activated charcoal material for absorbing components of flatus.

* * * * *